(12) United States Patent
Kobayashi et al.

(10) Patent No.: US 6,881,568 B2
(45) Date of Patent: Apr. 19, 2005

(54) METHOD FOR PROCESSING FORMALIN-FIXED ORGANIC WASTE AND AN APPARATUS THEREFOR

(75) Inventors: Tadao Kobayashi, Shiga (JP); Kohei Nozawa, Ibaragi (JP); Susumu Kato, Osaka (JP)

(73) Assignees: Sanyo Electric Co., Ltd., Osaka (JP); Sanyo Electric Biomedical Co., Ltd., Osaka (JP)

( * ) Notice: Subject to any disclaimer, the term of this patent is extended or adjusted under 35 U.S.C. 154(b) by 0 days.

(21) Appl. No.: 10/677,476

(22) Filed: Oct. 3, 2003

(65) Prior Publication Data

US 2004/0209347 A1 Oct. 21, 2004

(30) Foreign Application Priority Data

Oct. 3, 2002 (JP) .................................... 2002-291460

(51) Int. Cl.[7] .............................................. B09B 3/00
(52) U.S. Cl. .................... 435/262; 435/262.5; 210/632; 210/749
(58) Field of Search ................................. 210/606, 612, 210/632, 749, 761; 435/262, 262.5

(56) References Cited

U.S. PATENT DOCUMENTS

| | | | | |
|---|---|---|---|---|
| 4,104,162 A | * | 8/1978 | Junkermann et al. | 210/759 |
| 4,157,300 A | * | 6/1979 | Junkermann et al. | 210/754 |
| 5,723,049 A | * | 3/1998 | Weisenfeld | 210/758 |

* cited by examiner

Primary Examiner—David A. Redding
(74) Attorney, Agent, or Firm—McDermott Will & Emery LLP

(57) ABSTRACT

It is an object to provide an organic waste processing method and apparatus capable of making a formalin nontoxic and decreasing an amount and/or a volume of a formalin-fixed organic waste easily in a shorter time without retaining an original form.

A formalin-fixed organic waste processing method comprising the steps of formalin neutralizing a formalin-fixed organic waste, decomposing the waste using an enzyme, and subsequently, carrying out a drying process, and an organic waste processing apparatus comprising a processing chamber 2 for processing the waste, a stirring paddle provided in the processing chamber 2, a driving motor of the paddle, a heater 5 for the processing chamber 2, air supply means 6, exhaust means 14, and control means 7 for controlling the operations of the driving motor, the heater 5, the air supply means 6 and the exhaust means 14.

15 Claims, 5 Drawing Sheets

METHOD FOR PROCESSING FORMALIN-FIXED ORGANIC WASTE AND AN APPARATUS THEREFOR

BACKGROUND OF THE INVENTION

1. Technical Field to which the Invention Belongs

The present invention relates to a method for processing a formalin-fixed organic waste and an apparatus therefor, and more particularly, to a method of processing a formalin-fixed organic waste which processes the formalin-fixed organic waste in three stages including a formalin neutralizing process, a decomposing process and a drying process, and a processing apparatus capable of implementing the same.

2. Prior Art and Problems that the Invention is to Solve

Conventionally, internal organs or the like generated after an operation or an autopsy in a hospital have been formalin-fixed and stored for a constant period and have been then incinerated in a funeral hall or the disposal of an infectious waste has been entrusted to a trader. However, storage and disposal in the hospital have been obliged to be carried out by a disposal capability in the funeral hall or the like.

On the other hand, the burning of a formalin damages the furnace of an incinerating place, and furthermore, a moisture per unit weight is very large. For this reason, dioxin is generated by low-temperature burning depending on an incinerating apparatus.

In some cases, accordingly, the formalin is volatilized and dried in the sun or by means of an oven and the incinerating process is then carried out. However, there is a problem in that the formalin to be a toxic substance deteriorates a working environment beyond a regulated concentration and a great deal of time and labor is required. Under present conditions, thus, a method of efficiently processing formalin-fixed internal organs has not been established.

In consideration of the problems, it is an object of the present invention to provide a processing method capable of suppressing the influence of the formalin on a human body and sufficiently decreasing the amount and volume of an organic waste which does not retain an original form but is formalin-fixed in a simple and shorter work, and an apparatus therefore.

SUMMARY OF THE INVENTION

The present invention provides a formalin-fixed organic waste processing method in which a formalin-fixed organic waste is subjected to a formalin neutralizing process and is then subjected to a decomposing process by using an enzyme, and subsequently, a decomposed substance thus obtained is subjected to a drying process.

Moreover, the present invention provides a formalin-fixed organic waste processing method in which a formalin-fixed organic waste is processed by using a neutralizing and decomposing agent capable of neutralizing a formalin and dissolving an organic substance, and subsequently, is subjected to a drying process.

From another viewpoint, furthermore, the present invention provides an organic waste processing apparatus comprising a processing chamber for processing a formalin-fixed organic waste, a stirring paddle for stirring the organic waste in the processing chamber, a driving motor for driving the stirring paddle, a heater for heating an inside of the processing chamber, air supply means for supplying air in the processing chamber, exhaust means for discharging a gas in the processing chamber, and control means for controlling operations of the driving motor, the heater, the air supply means and the exhaust means in order to formalin-neutralize the organic waste in the processing chamber under heating, to then decompose the organic waste thus neutralized by using an enzyme supplied into the processing chamber, and to thereafter dry the decomposed substance and to discharge a gas generated at that time.

DETAILED DESCRIPTION OF THE PREFERRED EMBODIMENTS

Figure 1:
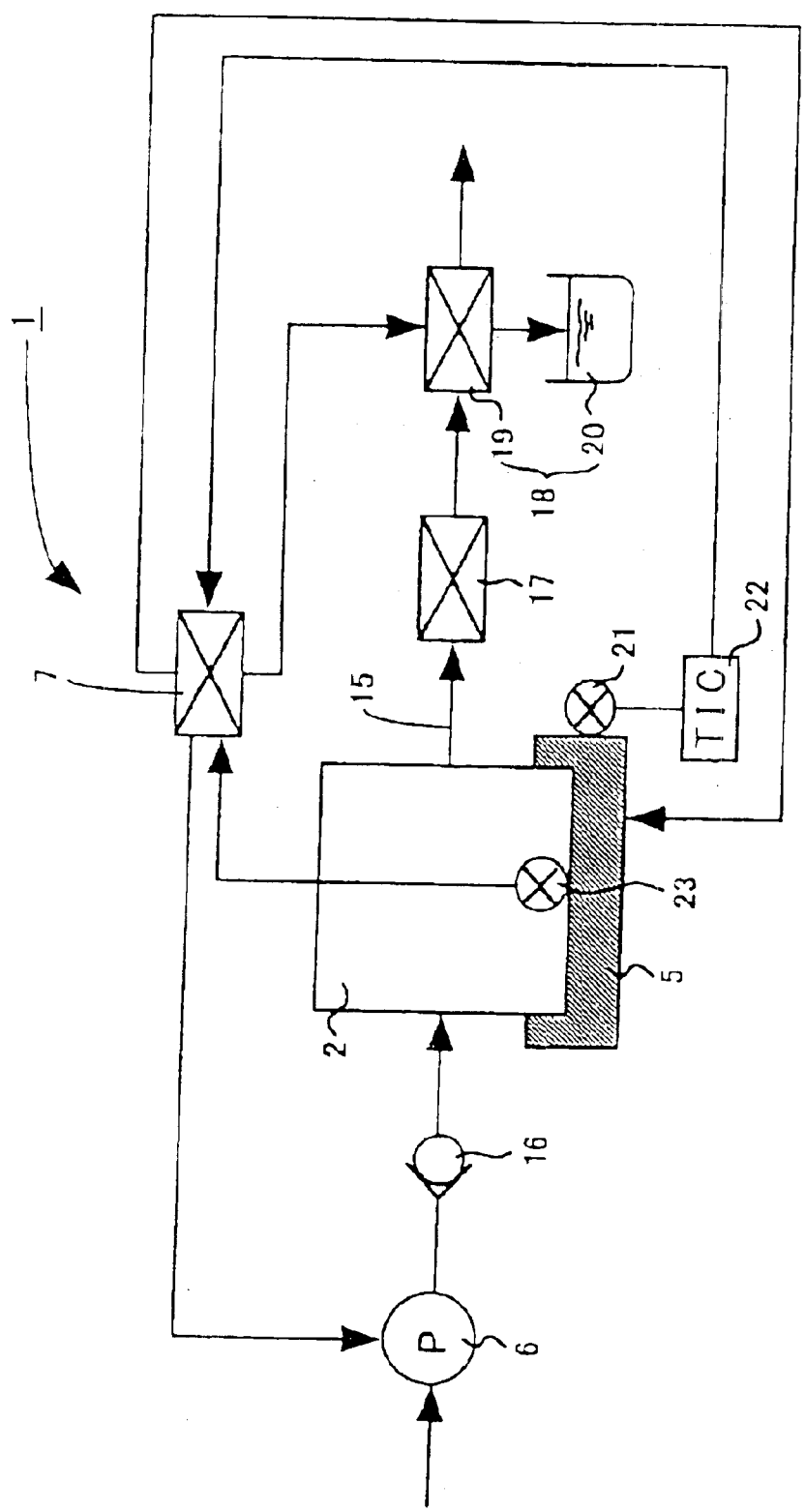
FIG. 1 is an explanatory diagram schematically showing the whole structure of an apparatus for processing an organic waste according to an embodiment of the present invention.

An organic waste which is formalin-fixed in the present invention typically represents internal organs subjected to a pathological test which is removed by an operation, an autopsy or the like in a hospital, and usually includes all internal organs excluding a bone, and specifically, various internal organs such as a fibroid having a hardness, the mesentery having a rich fat tissue and a mammectomy tissue. These internal organs may be obtained by washing a formalin-fixing solution in water, may be maintained in an exact state which is formalin-fixed without washing in water, or may be packed in a vacuum and set in a state in which a bag is not broken.

A formalin neutralizing process can be carried out by optionally heating an organic waste and causing a formalin neutralizer to come in contact with the organic waste. In particular, it is preferable that the formalin neutralizer is added and be caused to come in contact while heating. In order to uniformly cause the formalin neutralizer to come in contact with an organic waste during the formalin neutralizing process, furthermore, it is also possible to add accessory materials such as a proper amount of wood chip and/or water.

For the formalin neutralizer, for example, a chemical substance capable of promoting the decomposition of a formalin is not particularly restricted but it is preferable that the substance does not adversely affect an environment but is safe and easy to handle. More specifically, an alkali compound such as slaked lime, sodium hydroxide, potassium hydroxide, sodium hypochlorite or ammonia water can be used. These may be a solution, a suspension or a solid substance (powder, granule, tablets or the like) molded together with a proper carrier. For example, it is proper that the formalin neutralizer is used for an organic waste in approximately 1 to 5% by weight. In the case in which strong alkali such as sodium hydroxide is used, particularly, an organic waste can also be dissolved with the neutralization of a formalin, and a subsequent decomposing process using an enzyme can be omitted.

The formalin neutralizing process can be carried out by at least causing the formalin neutralizer to come in contact with the organic waste, and furthermore, is preferably carried out under a stirring and shearing load. In other words, in a decomposing process which will be described below, it is preferable that the shearing is also carried out by stirring during the stirring in such a manner that the organic waste can be decomposed by the enzyme sufficiently and effectively. The stirring and shearing load can be carried out by using stirring means of a paddle type which will be described below, for example.

It is preferable that the stirring and shearing load is properly carried out in such a manner that the organic waste can come in contact with the formalin neutralizer uniformly and sufficiently. For example, in the case in which the stirring means of a paddle type is used, approximately 1 to 10 rotations/minute, and preferably, approximately 1 to 5 rotations/minute can be applied. At this time, the stirring may be carried out continuously or intermittently.

It is proper that the formalin neutralizing process is carried out until a formalin concentration in a processing chamber obtained after the formalin neutralizing process reaches 0.1 ppm or less and preferably a detection limit or less in consideration of the amount of an organic waste to be processed, the size of the processing chamber to be used, an outside air temperature, the amount of the formalin neutralizer or the like, for example. More specifically, in the case in which approximately 5 to 6 kg of an organic waste is put in a processing chamber for approximately 10 to 20 liters, it is proper that the process is carried out for approximately 2 to 15 hours, and preferably 2 to 8 hours. Consequently, the formalin extracted from the organic waste to a water fraction can be decomposed by the formalin neutralizer.

It is preferable that the formalin neutralizing process is heated to a temperature at which deformalization and formalin decomposition from the organic waste can be efficiently carried out in order to shorten a time required for the process. It is proper that a heating temperature is set within approximately 50 to 90° C., for example, and the decomposition of a formalin is acceleratingly promoted at a temperature of approximately 55° C. or more. The temperature range implies the temperature range of the organic waste itself to be processed. In order to carry out the formalin neutralizing process within such a temperature range, as will be described below, there are employed a method of heating a processing chamber itself by means of a heater, a method of supplying air having a temperature regulated, and the like.

The end of the formalin neutralizing process can be determined by utilizing pH of an organic waste, a time required for the process, a formalin concentration detecting sensor provided in the processing chamber and the like. It is also possible to determine the end at a proper time by setting, as standards, the amount of the organic waste to be used, the amount of the formalin neutralizer to be used, the time required for the processing and the like.

In the formalin neutralizing process, it is not necessary to positively discharge a gas in the processing chamber. For example, it is preferable to nonforcibly carry out an evacuation by the expansion of the gas in the processing chamber which is caused by the heating.

In the present invention, a secondary neutralizing process may be further carried out before the decomposing process using an enzyme after the formalin neutralizing process. The secondary neutralizing process can be carried out by adding a secondary neutralizer such as hydrocarbon, for example, monosaccharides, a carbonate compound, or the like. The amount of the secondary neutralizer can be properly regulated in consideration of the amount of the organic waste to be used, the type and amount of the formalin neutralizer, the time of the formalin neutralizing process and the like. The secondary neutralizing process can consume the amount of the excessive formalin neutralizer for the organic waste almost completely and can effectively prevent a reduction in an enzymatic activity to be subsequently used or the acceleration of a deactivation speed. Consequently, it is possible to increase the degree of freedom for setting the range of the amount, type and configuration of the organic waste to be processed at a time, the amount of the formalin neutralizer to be used for one process, a time required for the formalin neutralizing process and the like, and it is possible to more reliably decrease the amount and/or volume of the organic waste.

Also in the secondary neutralizing process, as described above, it is preferable that an evacuation should be nonforcibly carried out by the gas expansion in the processing chamber.

After the formalin neutralizing process, the organic waste is subjected to the decomposing process by using the enzyme. The enzyme can properly be selected depending on the type of the organic waste to be processed. For example, protease, peptidase, elastase and/or lipase are/is proper, and alkali protease is particularly preferable. In another respect, moreover, it is proper to use any or all enzyme(s) having an alkali property with optimum pH which is/are rarely influenced by an activity thereof also under the presence of sodium or potassium in a high concentration and which is/are greatly resistant to heat. More specifically, it is possible to use such an enzyme as to produce various microorganisms, for example, *Bacillus*group or *Streptomyces* group which is put on the market. For example, it is possible to use Proleather-FG-F (produced by Amano Enzyme Co., Ltd.), PROTEASE S "AMANO" G (produced by Amano Enzyme Co., Ltd.) and the like. The enzyme may be used by a combination of at least two of a type, optimum pH, an optimum temperature, an activity based on a difference in an environment, a decomposing object and the like. The enzyme may be used in any configuration, and preferably, powder, granule, a tablet or a solid. In particular, it is preferable that the powder, the granule or the tablet is easily put in the processing chamber of an organic waste and the enzyme should be accommodated in a water-soluble or fragile container by directly coming in contact with a formalin having a high concentration present in the processing chamber so as not to deteriorate the activity of the enzyme. Moreover, it is preferable that the amount of the solid per time is molded to one piece with a carrier or the molded substance is coated with the carrier or the like such that a direct contact with the formalin of the enzyme can be suppressed as much as possible. Examples of the water-soluble or fragile container may use PVA, gelatin, cellulose, a paper pulp and the like.

The amount of the enzyme can be properly regulated depending on the type and amount of the organic waste, the type and amount of the formalin neutralizer, the time required for the formalin neutralizing process, the presence of the secondary neutralizing process and the like. For example, it is proper that the enzyme is used in a rate of approximately 0.05 to 10.0% by weight for the organic waste to be processed, particularly, approximately 0.1 to 5.0% by weight in case of Proleather-FG-F.

When using the enzyme, it is also possible to use an enzyme stabilizer at the same time. Examples of the enzyme stabilizer include a pH buffering agent, a surface active agent and the like. The amount of the enzyme stabilizer to be used can be properly regulated depending on the type and amount of the enzyme to be used and the like.

The decomposing process using the enzyme can be carried out without heating or by the heating, and it is proper that the same decomposing process is carried out in the vicinity of the optimum temperature of the selected enzyme. For example, a temperature range of approximately 35 to 70° C. can be used. It is preferable that the decomposing process is carried out under a mixture, stirring or stirring and shearing load in the same manner as the formalin neutralizing process.

Although the end of the decomposing process can be determined by a visual observation, a paddle rotation resistance or the like, it may be determined at a proper time by setting, as standards, the amount of the used organic waste, the amount of the used enzyme, the processing time or the like. For example, while the end can be properly regulated depending on the amount of the organic waste, the type and amount of the used enzyme or the like, approximately 1 to 10 hours, and preferably, approximately 2 to 6 hours can be applied.

Also in the decomposing process, it is preferable that air is nonforcibly discharged by a gas expansion in the processing chamber as described above.

After the decomposing process, a substance to be decomposed is usually brought into a state having a fluidity in which a solid substance is contained, and the substance to be decomposed is dried. The drying process can be carried out by heating the processing chamber itself, supplying a gas having a temperature and/or a humidity regulated to the processing chamber or their combination. It is preferable that the drying process is carried out by heating to approximately 40 to 80° C.

It is preferable that the drying process is carried out under a stirring or stirring and shearing load in the same manner as the formalin neutralizing process.

The end of the drying process can be determined by a visual observation, a moisture content sensor provided in the processing chamber, or the like. The end may be determined at a proper time by setting, as standards, the amount of the used organic waste, a drying temperature, a drying time and the like. For example, while a regulation can properly be carried out depending on the amount of the organic waste, the drying temperature or the like, approximately 2 to 15 hours, particularly, approximately 4 to 8 hours are suitable. Moreover, a time that a moisture content is approximately 5 to 20%, particularly, approximately 10% is suitable.

It is preferable that the drying process can be promoted by positively discharging a steam in the processing chamber to an outside thereof, and a gas is positively supplied from air supply means provided in the processing chamber to positively discharge the steam from exhaust means as will be described below.

It is preferable that the organic waste having an amount and/or volume reduced which is obtained by the method according to the present invention is taken out of the processing chamber immediately after the drying or after cooling and should be incinerated.

Moreover, the apparatus for processing the organic waste according to the present invention can implement the processing method and comprises a processing chamber for processing the organic waste which is formalin-fixed.

The processing chamber is to have an airtightness to prevent a formalin gas to be a powerful drug giving out an irritating smell from leaking to an outside. For example, it is proper that the processing chamber employs a double opening and closing structure in a put-in portion for putting in the formalin-fixed organic waste or the like, a portion for taking out the organic waste obtained after the processing and the like, and employs a seal structure in air supply means, exhaust means, a pivotal support portion of a stirring paddle and the like which will be described below.

The size of the processing chamber is not particularly restricted but can be usually set to have a capacity (for example, 10 to 30 liters) in consideration of employment in a hospital, a research institute or the like.

The processing chamber having such a structure is provided with a stirring paddle for stirring the organic waste in the processing chamber and a driving motor for driving the stirring paddle.

The stirring paddle has such a structure that the organic waste in the processing chamber can be stirred to apply a shearing load by a rotation. More specifically, it is preferable that the stirring paddle includes a rotary shaft supported pivotally on the processing chamber, a plurality of (for example, 6 to 12) vertical blades protruded with an interval in an almost axial direction from the rotary shaft, and a horizontal blade protruded from the vicinity of the tip of the vertical blade to be a free end and having a tip portion coupled every set made by two horizontal blades, and that the rotary shaft is rotated (rotated, normally or reversely rotated or rocked) by means of the driving motor.

The processing chamber is provided with an organic waste heater for heating the organic waste in the processing chamber.

The organic waste heater is provided for processing respective processing objects under heating in a process such as a formalin neutralizing process, a decomposing process using an enzyme or a drying process. Preferably, an electric heater or the like is attached to the whole bottom portion of the outside of the processing chamber in such a manner that a heat can be transferred to a processing object.

There is provided the air supply means for supplying air into the processing chamber. The air supply means is mainly provided for supplying air required in the process, for example, the neutralizing process, the decomposing process and/or the drying process, particularly, the drying process or for discharging the air generated in the processing chamber to the exhaust means. More specifically, a pressurizing type pump or a sirocco fan is preferable and a corrosion-resisting diaphragm pump is more preferable. It is preferable that a check valve for preventing a back flow from the inside of the processing chamber is provided between the air supply means and the processing chamber in order to prevent the back flow of a formalin gas or another harmful gas.

The processing chamber is provided with the exhaust means for mainly discharging a gas in the processing chamber in order to discharge a steam generated in the processing chamber, and secondarily, a residual formalin gas, a harmful gas generated after the formalin neutralizing process or the like and/or to carry out a nontoxicity process.

More specifically, the exhaust means is formed by an exhaust path for nonforcibly discharging the gas in the processing chamber (see FIG. 3) or the exhaust path and a nontoxic dehumidifying vessel interposed in the exhaust path and serving to make a discharged gas nontoxic and to carry out a dehumidification (see FIG. 2), or the like.

The nontoxic dehumidifying vessel is constituted by a catalyst processing vessel for making the discharged gas nontoxic, and a condensing and removing vessel for condensing and removing at least a moisture in an exhaust gas (see FIG. 1).

It is preferable that the catalyst processing vessel includes at least a catalyst capable of removing the smell of a residual formalin gas. More specifically, for the catalyst, a platinum catalyst is carried out on a carrier having a honeycomb structure of ceramics, and furthermore, well-known catalysts in the field can be used.

On the other hand, it is preferable that the condensing and removing vessel is constituted by a condenser (a KONDENSA or a radiator fin) for condensing at least a moisture in a discharged gas (containing other harmful gases) and a tank for storing a condensate which is obtained.

It is preferable that the processing apparatus according to the present invention comprises automatic supply means for automatically putting, into the processing chamber, a secondary neutralizer or an enzyme to be used in the secondary neutralizing process or the decomposing process using the enzyme. For example, it is possible to use a dispenser (a supply unit or a supply device) to be usually utilized for automatically supplying a predetermined amount of drug or chemical material at a predetermined time in the field.

Furthermore, the internal wall surface of the processing chamber is provided with a moisture content sensor for sensing the moisture content of a decomposed substance in the drying process and sending a sensing signal to control means which will be described below. Consequently, the drying process can be carried out efficiently and easily. More specifically, the bottom face of the internal wall of the processing chamber is caused to have a semicircular section so that the moisture content sensor can be provided within a range of an angle of 45 degrees from the lowest portion of the bottom face of the internal wall.

Moreover, there is provided control means for controlling the operations of the driving motor, the heater, the air supply means, the exhaust means and the like. The control means can be generally constituted by an electronic circuit, a control circuit, a processor, a microcomputer or the like. By the control means, the operation of each of the components can be controlled. Consequently, it is possible to carry out a formalin neutralizing process over an organic waste in the processing chamber under heating, then decompose the organic waste thus neutralized through an enzyme fed into the processing chamber, thereafter dry the decomposed substance and discharge a gas generated at that time. As a result, the formalin gas can be decomposed and made nontoxic, and furthermore, the amount and volume of the organic waste can be automatically decreased in a drying state in a short time without retaining an original form.

An embodiment of an organic waste processing apparatus and method according to the present invention will be described below with reference to the drawings.

Figure 2:
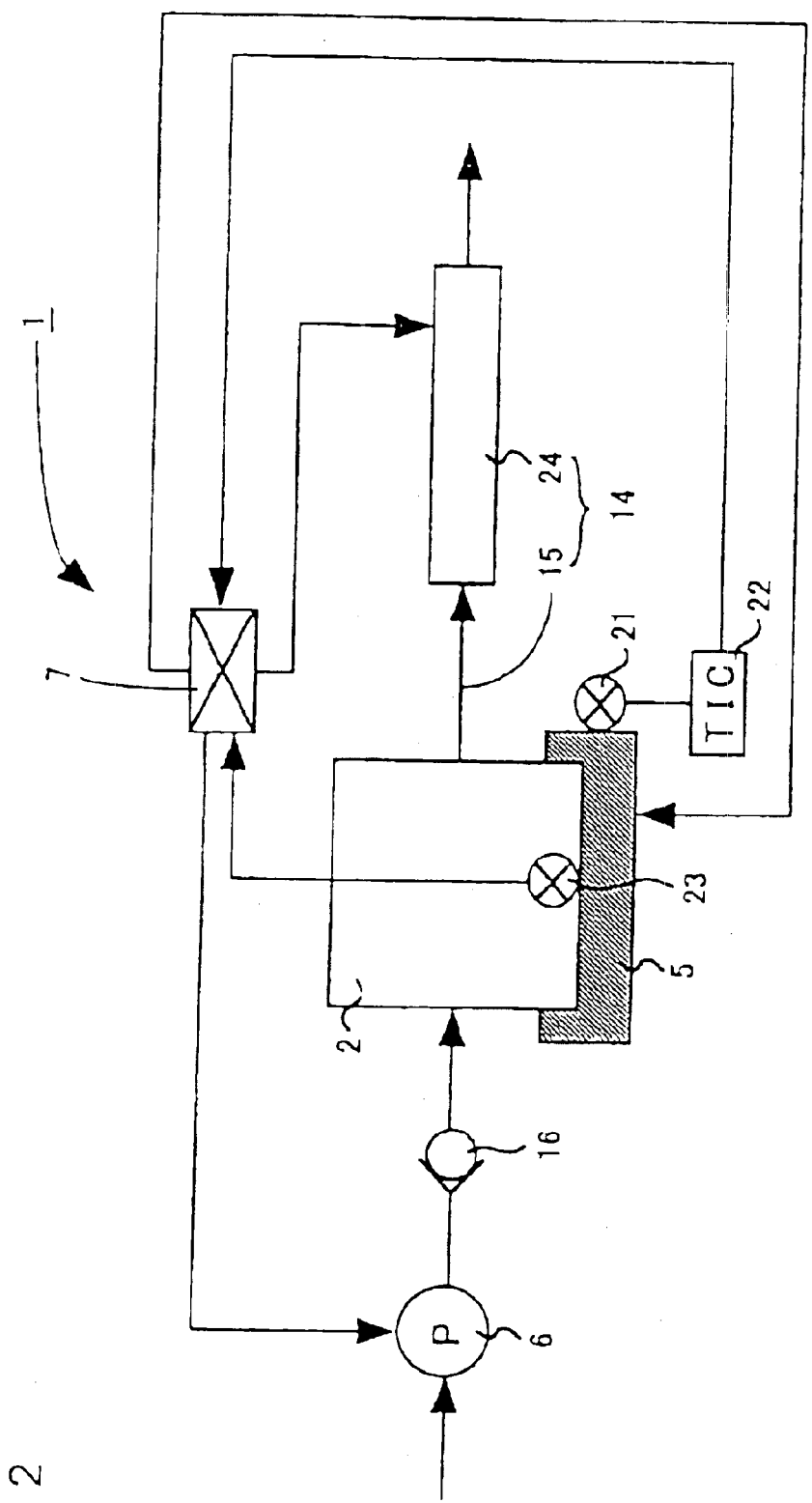
FIG. 2 is an explanatory diagram schematically showing the whole structure of an apparatus for processing an organic waste according to another embodiment of the present invention.
Figure 3:
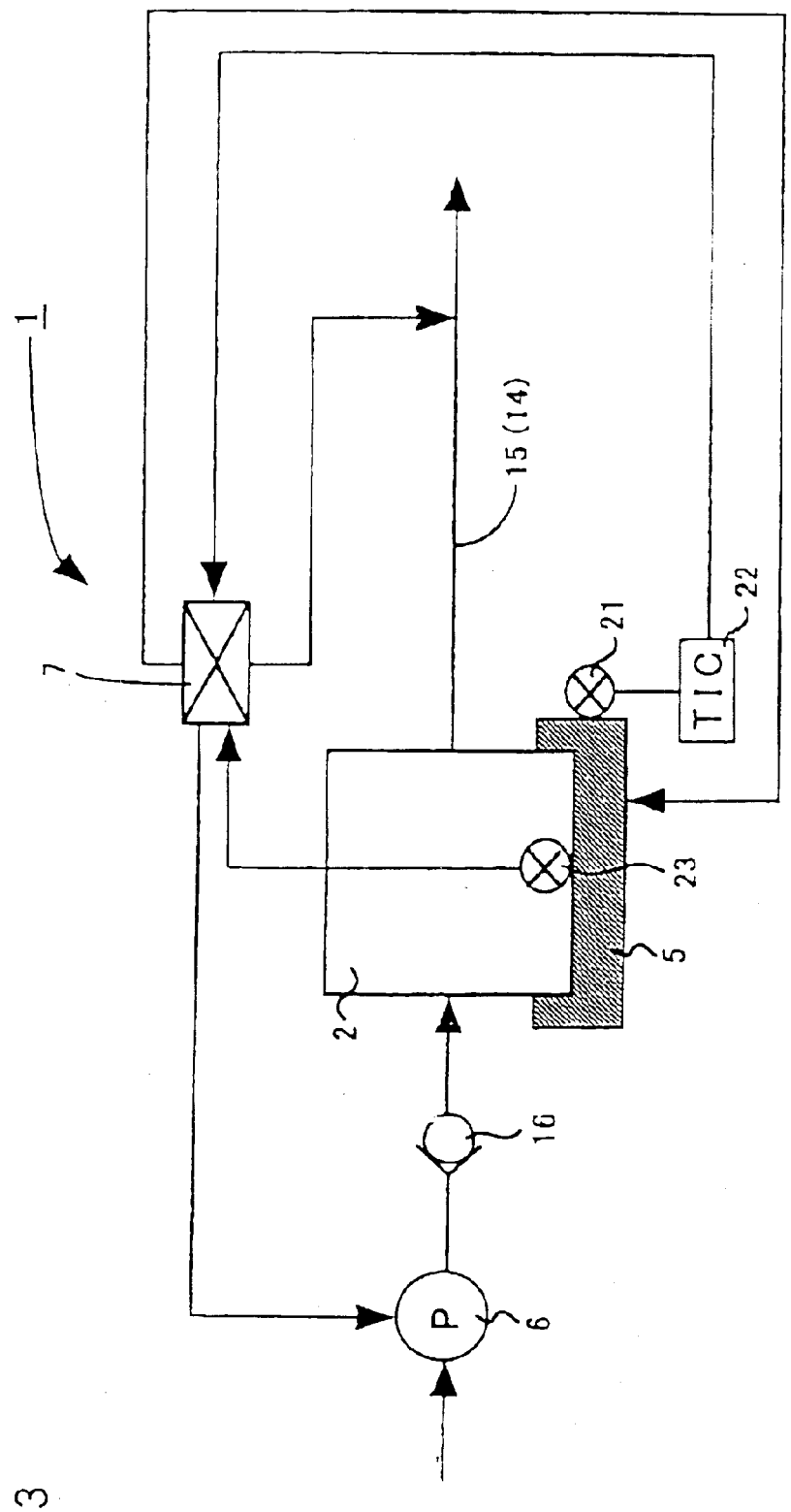
FIG. 3 is an explanatory diagram schematically showing the whole structure of an apparatus for processing an organic waste according to a further embodiment of the present invention.
Figure 4:
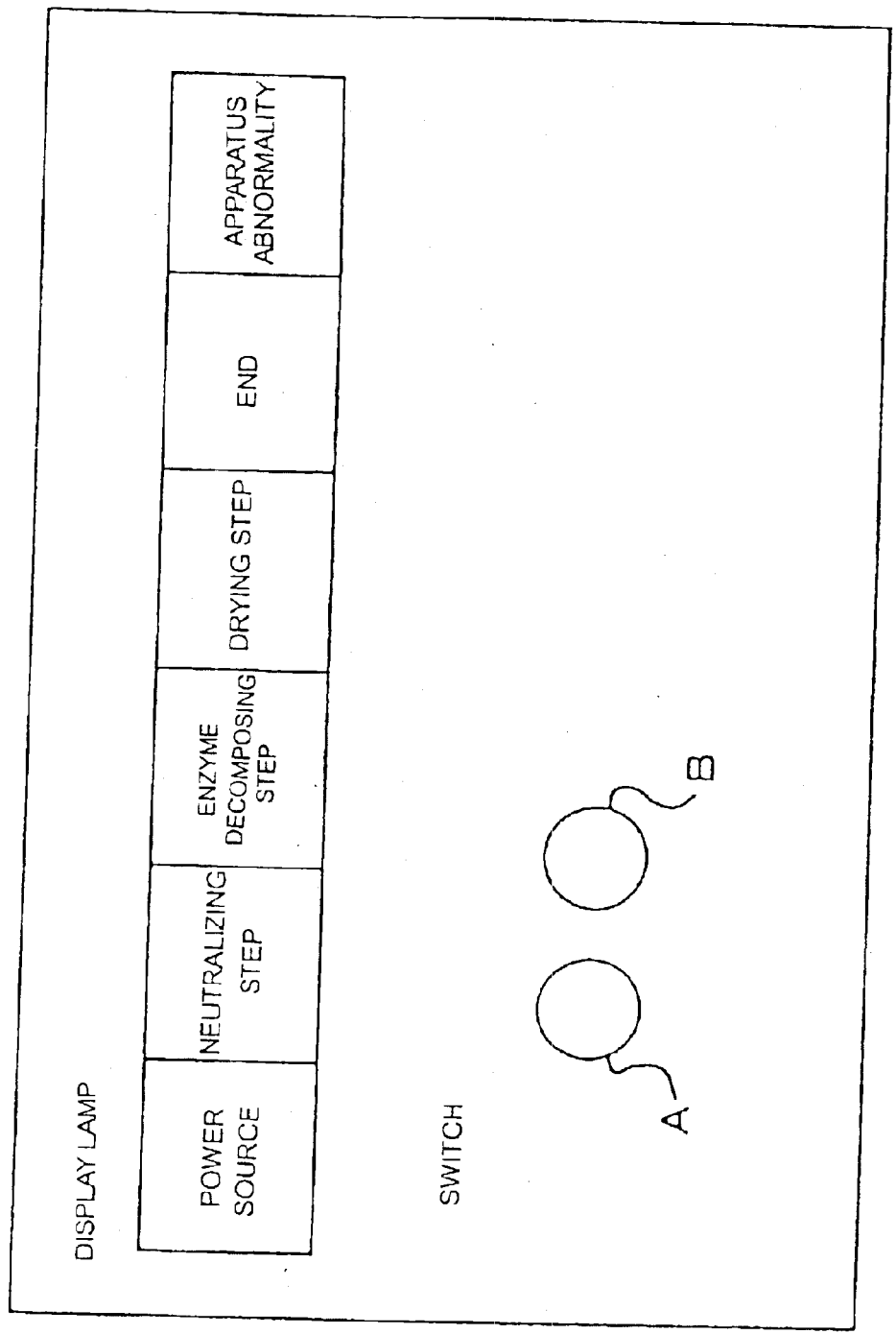
FIG. 4 is an explanatory diagram showing the arrangement of a display lamp and a switch to be used for each of the processing apparatuses in FIGS. 1 to 3.
Figure 5:
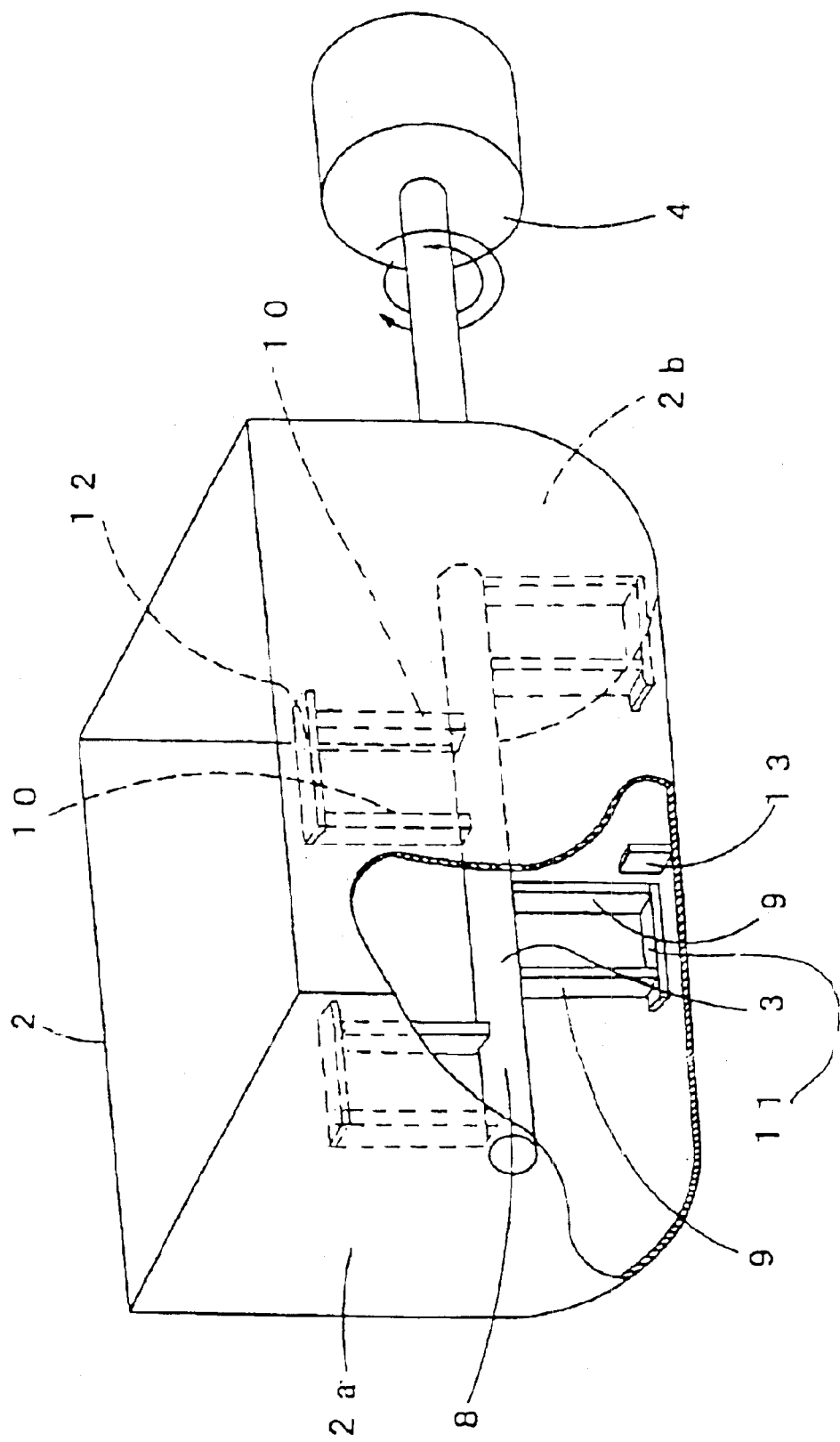
FIG. 5 is an explanatory view showing the schematic structure of a processing chamber in FIGS. 1 to 3.

FIGS. 1 to 3 are explanatory diagrams schematically showing the whole structure of the organic waste processing apparatus according to the present invention, FIG. 4 is an explanatory diagram showing the arrangement of a display lamp and a switch, and FIG. 5 is a perspective view for explaining a processing chamber.

As shown in FIGS. 1 to 3 and 4, an organic waste processing apparatus 1 is mainly constituted by a processing chamber 2 for putting in a formalin-fixed organic waste and processing the organic waste thus put in, a stirring paddle 3 supported pivotally in the processing chamber 2 and serving to stir the organic waste, a driving motor 4 for driving the stirring paddle 3, a heater 5 provided in contact with a bottom portion in the processing chamber 2 to transfer a heat thereto and serving to heat the organic waste, a corrosion-resisting diaphragm pump 6 to be air supply means for supplying air into the processing chamber 2, exhaust means 14 for discharging a gas in the processing chamber 2, and a control circuit 7 to be control means.

The processing chamber 2 is box-shaped and is constituted to prevent a formalin gas from leaking, and has a lower half part formed to be semicylindrical with a central axis set to be horizontal (the bottom face of an internal wall has a semicircular section) and the stirring paddle 3 is rotatably supported on flat and vertical walls 2a and 2b which are opposed to each other.

The stirring paddle 3 is constituted by a rotary shaft 8, vertical blades 9 and 9, 10 and 10, . . . provided to have an interval in an almost axial direction from the rotary shaft 8, and horizontal blades 11, 12, . . . coupling the vicinity of the tips of the vertical blades 9 and 10, and the rotary shaft 8 is pivotally supported around the semicylindrical portion of the processing chamber 2 and the horizontal blades 11, 12 . . . can be moved along the internal wall of the semicylindrical portion. The rotary shaft 8 is rotated by means of the driving motor 4 from the outside of the processing chamber 2. 13 denotes a fixed blade for breaking a substance to be processed by the mating of the vertical blades 9 and 10 and the horizontal blades 11 and 12 in the stirring paddle 3.

By the rotation of the stirring paddle 3, the organic waste in the processing chamber 2 is stirred, and particularly, the vertical blades 9, 9 and 10, 10 and the horizontal blades 11 and 12 are moved along the semicylindrical portion of the bottom part of the processing chamber 2. Therefore, the whole organic waste can be always stirred and a stirring efficiency can be enhanced. Furthermore, each of these blades is mated with the fixed blade 13 in the bottom portion of the processing chamber 2. Therefore, the breakage of the organic waste can also be promoted.

The exhaust means 14 is provided for discharging a gas from the processing chamber 2, and is constituted by an exhaust path 15 for nonforcibly discharging a gas in the processing chamber 2 as shown in FIG. 3. In order to mainly carry out a nontoxic processing over a harmful gas generated after the neutralizing process for a steam, optionally a residual formalin gas, a formalin or the like, moreover, the exhaust means 14 may be constituted by the exhaust path 15 and a nontoxic dehumidifying vessel 24 interposed in the exhaust path 15 and serving to make a discharged gas nontoxic and carry out a dehumidification as shown in FIG. 2, and furthermore, may be constituted by the exhaust path 15, and the nontoxic humidifying vessel 24 including a catalyst processing vessel 17 and a condensing and removing vessel 18 for condensing and removing at least a moisture in a discharged gas as shown in FIG. 1. The catalyst processing vessel 17 includes a platinum catalyst.

As shown in FIG. 1, the condensing and removing vessel 18 is constituted by a condenser 19 for condensing a moisture in a discharged gas, and a tank 20 for storing the condensate thus obtained.

A check valve 16 for preventing a back flow from the inside of the processing chamber 2 is provided between the corrosion-resisting diaphragm pump 6 and the processing chamber 2 to prevent the back flow of a formalin gas or the like.

Moreover, 21 denotes a temperature sensor and 22 denotes a TIC (thermal indicator control) for transmitting a temperature signal obtained by the temperature sensor 21 to the control circuit 7. 23 denotes a moisture content sensor.

The temperature signal and the moisture content signal thus obtained are transmitted to the control circuit 7 and a control signal is output from the control circuit 7 to the heater 5, the corrosion-resisting diaphragm pump 6, the driving motor 4 (which are not shown in FIGS. 1 to 3 in addition to the stirring paddle 3) and the like.

As described above, the operation of each structure of the processing apparatus 1 is controlled by the control circuit 7. More specifically, the control circuit 7 controls the operations of the driving motor 4, the heater 5, the corrosion-resisting diaphragm pump 6 and the exhaust means 14 so that the organic waste in the processing chamber 2 can be subjected to a formalin neutralizing process under heating, a decomposing process using an enzyme and a drying process, and a gas generated at that time is discharged.

The arrangement of a display lamp and a switch in an operation panel will be described with reference to FIG. 4.

First of all, a main power switch is provided in a distant position (not shown). When the main power switch is turned ON, a display lamp of "power" in FIG. 4 is turned ON. When a switch A is pressed down, a display lamp of "a neutralizing step" is turned ON so that a process is started. When the process proceeds (ends), lighting is carried out in order of the "neutralizing step", an "enzyme decomposing step", a "drying step" and "end". If any abnormality is generated, a display lamp of "apparatus abnormality" is turned ON together with a buzzer if necessary so that the processing step is stopped. By operating a switch B, moreover, it is also possible to emergently stop equipment artificially.

Specific description will be given to a method of processing a formalin-fixed organic waste by using the apparatus described above.

The setting of decomposing conditions was investigated by using, as a formalin-fixed organic waste, the internal organs of a pig which are fixed in a 20% formalin solution and are obtained with the passage of three days to one week after the fixation. Consequently, an evaluation test using actual organic and fat tissues and the like was carried out based on the determined decomposing conditions in the Saiseikai Shiga Hospital.

First of all, 6 kg (approximately 12 liters) of internal organs to be a formalin-fixed organic waste, 5 liters of tap water, 130 g of slaked lime to be a formalin neutralizer and 1 kg (approximately 6 liters) of a wood chip to be an assistant material were put in the processing chamber 2 (a capacity of 30 liters) of the apparatus shown in FIG. 1.

For the formalin neutralizing process, the temperature of the organic waste itself in the processing chamber was held at 60 to 70° C. and was maintained for approximately 4 hours while carrying out stirring and shearing by the rotation of the stirring paddle 3 at two rotations/minute. Consequently, the formalin reacts to the slaked lime, and is saccharified and is made nontoxic. A gas generated in the processing chamber 2 passes through the exhaust path 15 and reaches the catalyst processing vessel 17 with a rise in an internal pressure of the inside of the processing chamber by heating, and the formalin gas is deodorized, and furthermore, a moisture present in the gas is condensed and removed by the condenser 19 and is then discharged to the air. The formalin gas remaining in the processing chamber is also pushed out forcibly toward the exhaust path 15 by the exhaust means 14. Thus, the formalin neutralizing step is completed. The concentration of the formalin in the vessel after approximately four hours was decreased to 0.1 ppm or less.

After the end of the formalin neutralizing process, 100 g of an enzyme (Proleather-FG-F), 60 g of disodium hydrogenphosphate (produced by Wako Pure Chemical Industries, Ltd.) to be an enzyme stabilizer and 40 g of sodium dihydrogenphosphate (produced by the Wako Pure Chemical Industries, Ltd.) were added and the inside of the processing chamber 2 was held at approximately 60° C. for approximately six hours, and a decomposing process was thus carried out. Consequently, the internal organs were subjected to a zymolysis so that a state of fluidity containing a solid substance was brought.

Then, the inside of the processing chamber 2 was held at approximately 60° C. for 10 to 15 hours and a drying process was thus carried out.

The amount and volume of the decomposed substance obtained after the process were decreased to 1.9 kg (approximately 5 liters) and an approximately 10% of a moisture content was obtained, and an original form thereof was not observed. Moreover, the smell of the decomposed substance obtained after the process was rarely obtained.

According to the example, the amount and the volume could be similarly decreased in any tissue irrespective of the type of a tissue such as a hard tissue or a fat tissue.

In particular, it is possible to carry out the formalin neutralizing process efficiently or in a short time by using the formalin neutralizer.

Also after any process, moreover, the detection of a microbe was not observed but a residual substance can be processed safely without contaminating an environment.

Advantage of the Invention

According to the present invention, the influence of a formalin on a human body can be suppressed and it is possible to process an organic waste without remaining an original form by a simple work in a short time. By using the formalin neutralizer, the formalin can be decomposed sufficiently and reliably, and furthermore, the tissue can be decomposed finely to more implement a decrease in the volume in a shorter time through the decomposing process using an enzyme. In addition, it is possible to more decrease an amount by drying the organic waste containing a large amount of water.

In the method according to the present invention, moreover, a final processed substance takes an appearance of so-called "soil", and it is possible to implement a processing method which is also coincident with a view of necrobiosis since ancient times and is easily accepted by the owner of the internal organs or relatives thereof.

In the case in which the formalin neutralizing process is to be carried out under heating and the case in which the organic waste is to be subjected to a formalin neutralizing process and a decomposing process using an enzyme under a stirring and shearing load, particularly, it is possible to implement a decrease in an amount and a volume in a shorter time.

By using alkali such as sodium hydroxide or potassium hydroxide for the formalin neutralizer, moreover, it is possible to dissolve the organic waste under a strong alkali environment and to carry out the decomposing process more efficiently.

According to the present invention, moreover, the formalin-fixed organic waste in the processing chamber can be subjected to the neutralizing process by the formalin neutralizer supplied into the processing chamber, and subsequently, the organic waste thus neutralized can be decomposed by an enzyme supplied into the processing chamber, and the drying process can be thereafter carried out. Therefore, a formalin gas giving an irritating smell by a powerful drug which is generated at that time can be made nontoxic and discharged, and furthermore, the amount and volume of the organic waste can be decreased in a drying state to anybody easily in a short time without retaining an original form.

Explanation of the Reference Designation 1 organic waste processing apparatus
2 processing chamber
2a, 2b vertical wall
3 stirring paddle
4 driving motor
5 heater
6 corrosion-resisting diaphragm pump (air supply means)
7 control circuit (control means)
8 rotary shaft
9 vertical blade
10 vertical blade
11 horizontal blade
12 horizontal blade
13 fixed blade
14 exhaust means
15 exhaust path (exhaust means)
16 check valve
17 catalyst processing vessel
18 condensing and removing vessel
19 condenser
20 tank
21 temperature sensor
22 TIC
23 moisture content sensor
24 nontoxicity dehumidifying vessel

What is claimed is:

1. A formalin-fixed organic waste processing method in which a formalin-fixed organic waste is subjected to a formalin neutralizing process and is then subjected to a decomposing process using an enzyme, and subsequently, a decomposed substance thus obtained is subjected to a drying process.

2. The method according to claim 1, wherein the formalin neutralizing process is carried out under heating by using a formalin neutralizer.

3. The method according to claim 1 or 2, wherein the organic waste is subjected to the formalin neutralizing process under a stirring and shearing load and the decomposing process using the enzyme.

4. The method according to claim 2, wherein the formalin neutralizer is slaked lime, sodium hydroxide or potassium hydroxide.

5. The method according to any of claim 1 or 2, wherein the formalin-fixed organic waste is an internal organ obtained by an operation or an autopsy.

6. A formalin-fixed organic waste processing method in which a formalin-fixed organic waste is processed by using a neutralizing and decomposing agent capable of neutralizing a formalin and dissolving an organic substance, and subsequently, is subjected to a drying process.

7. An organic waste processing apparatus comprising:
a processing chamber for processing a formalin-fixed organic waste;
a source of neutralizing enzymes;
a stirring paddle for stirring the organic waste in the processing chamber;
a driving motor for driving the stirring paddle;
a heater for heating an inside of the processing chamber;
air supply means for supplying air into the processing chamber;
exhaust means for discharging a gas in the processing chamber; and
control means for controlling operations of the driving motor, the heater, the air supply means, the source of neutralizing enzymes, and the exhaust means for formalin-neutralizing the organic waste in the processing chamber under heating, for then decomposing the organic waste thus neutralized by using an enzyme supplied into the processing chamber, for thereafter drying the decomposed substance, and for discharging a gas generated at that time.

8. The processing apparatus according to claim 7, wherein the exhaust means comprises an exhaust path for nonforcibly discharging the gas in the processing chamber, or the exhaust path and a nontoxicity dehumidifying vessel interposed in the exhaust path and serving to make the discharged gas nontoxic and carry out a dehumidification.

9. The processing apparatus according to claim 8, wherein the nontoxicity dehumidifying vessel includes a catalyst processing chamber for making the discharged gas nontoxic and a condensing and removing vessel for condensing and removing at least a moisture in the discharged gas.

10. The processing apparatus according to claim 9, wherein the catalyst processing chamber includes a catalyst for deodorizing at least a residual formalin gas.

11. The processing apparatus according to claim 9, wherein the condensing and removing vessel comprises a condenser for condensing at least a moisture in the discharged gas and a tank for storing a condensate thus obtained.

12. The processing apparatus according to any one of claims 7 to 11, wherein an internal wall surface of the processing chamber further comprises a moisture content sensor for sensing a moisture content of a decomposed substance in a drying process and sending a sensing signal to the control means.

13. The processing apparatus according to claim 12, wherein a bottom face of an internal wall of the processing chamber has a semicircular section and the moisture content sensor is provided within a range of an angle of 45 degrees from the lowest part on the bottom face of the internal wall.

14. The processing apparatus according to any one of claims 7 to 11, wherein the stirring paddle comprises a rotary shaft, a plurality of vertical blades protruded with an interval in an almost axial direction from the rotary shaft, and horizontal blades protruded from the vicinity of tips of the vertical blades to be free ends or to couple tip portions for each set, two horizontal blades making a pair.

15. The processing apparatus according to any one of claims 7 to 11, further comprising a check valve for preventing a back flow from the inside of the processing chamber between the processing chamber and the air supply means.

* * * * *